US00PP27785P2

(12) United States Plant Patent
Scheffers

(10) Patent No.: US PP27,785 P2
(45) Date of Patent: Mar. 14, 2017

(54) ***DRACAENA FRAGRANS* PLANT NAMED 'DRADORCO'**

(50) Latin Name: *Dracaena fragrans*
Varietal Denomination: Dradorco

(71) Applicant: Ruud Scheffers, Honselersdijk (NL)

(72) Inventor: Ruud Scheffers, Honselersdijk (NL)

(73) Assignee: Dragontree Beheer BV, Honselersdijk (NL)

( * ) Notice: Subject to any disclaimer, the term of this patent is extended or adjusted under 35 U.S.C. 154(b) by 0 days.

(21) Appl. No.: 14/756,772

(22) Filed: Oct. 9, 2015

(51) Int. Cl.
*A01H 5/12* (2006.01)

(52) U.S. Cl.
USPC ..... Plt./383

(58) Field of Classification Search
USPC ..... Plt./383
See application file for complete search history.

*Primary Examiner* — Annette Para
(74) *Attorney, Agent, or Firm* — Samuel R. McCoy, Jr.

(57) ABSTRACT

'Dradorco' is a new and distinctive variety of *Dracaena fragrans* which is characterized by a short and compact growth habit, a distinctive spiraling of the leaves, prominent golden leaf margins, and the stability of all characteristics from generation to generation. The new variety is typically produced as an indoor ornamental plant.

3 Drawing Sheets

Latin name of the genus and species:

The Latin name of the genus and species of the novel variety disclosed herein is *Dracaena fragrans*.

Variety denomination: The inventive variety of *Dracaena fragrans* disclosed herein has been given the variety denomination 'Dradorco'.

BACKGROUND OF THE INVENTION

The present invention relates to a new and distinct cultivar of *Dracaena fragrans*, which has been given the variety denomination of 'Dradorco'. Its market class is PLT/383.

Parentage: The new cultivar is the product of chance discovery. The new variety originated as one of a number of a naturally occurring, single branch mutations of *Dracaena fragrans* '2004031C' (U.S. Plant Pat. No. 24,796), discovered at the inventor's nursery in Honselersdijk, The Netherlands. Said mutations were harvested from the mother plant, rerooted, and then grown to a mature size. Once mature, each new variety was asexually propagated by stem cuttings, through two successive generations, to increase the number of plants for the purpose of evaluating the commercial value of each candidate. The resulting plants were then evaluated for one and a half years. In December of 2012, one of the candidates was selected for its compact size, spiraling foliage, and short leaves. The new cultivar was given the breeder denomination 'Dradorco'.

Asexual Reproduction: Asexual reproduction of 'Dradorco', by way of root stem cuttings, was first performed in the spring of 2010 at the inventor's nursery in Honselersdijk, The Netherlands. Successive generations so produced have shown that the unique features of the instant cultivar are stable and reproduced true to type.

SUMMARY OF THE INVENTION

The cultivar 'Dradorco' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Dracaena fragrans* cultivar 'Dradorco'. These traits, in combination, distinguish 'Dradorco' as a new and distinct cultivar.

1. *Dracaena* 'Dradorco' exhibits a short, compact growth habit; and
2. *Dracaena* 'Dradorco' exhibits short, erect leaves which are heavily spiraled along the midbrib; and
3. *Dracaena* 'Dradorco' exhibits a large area of golden coloration at and near the leaf margins.

Figure 1:
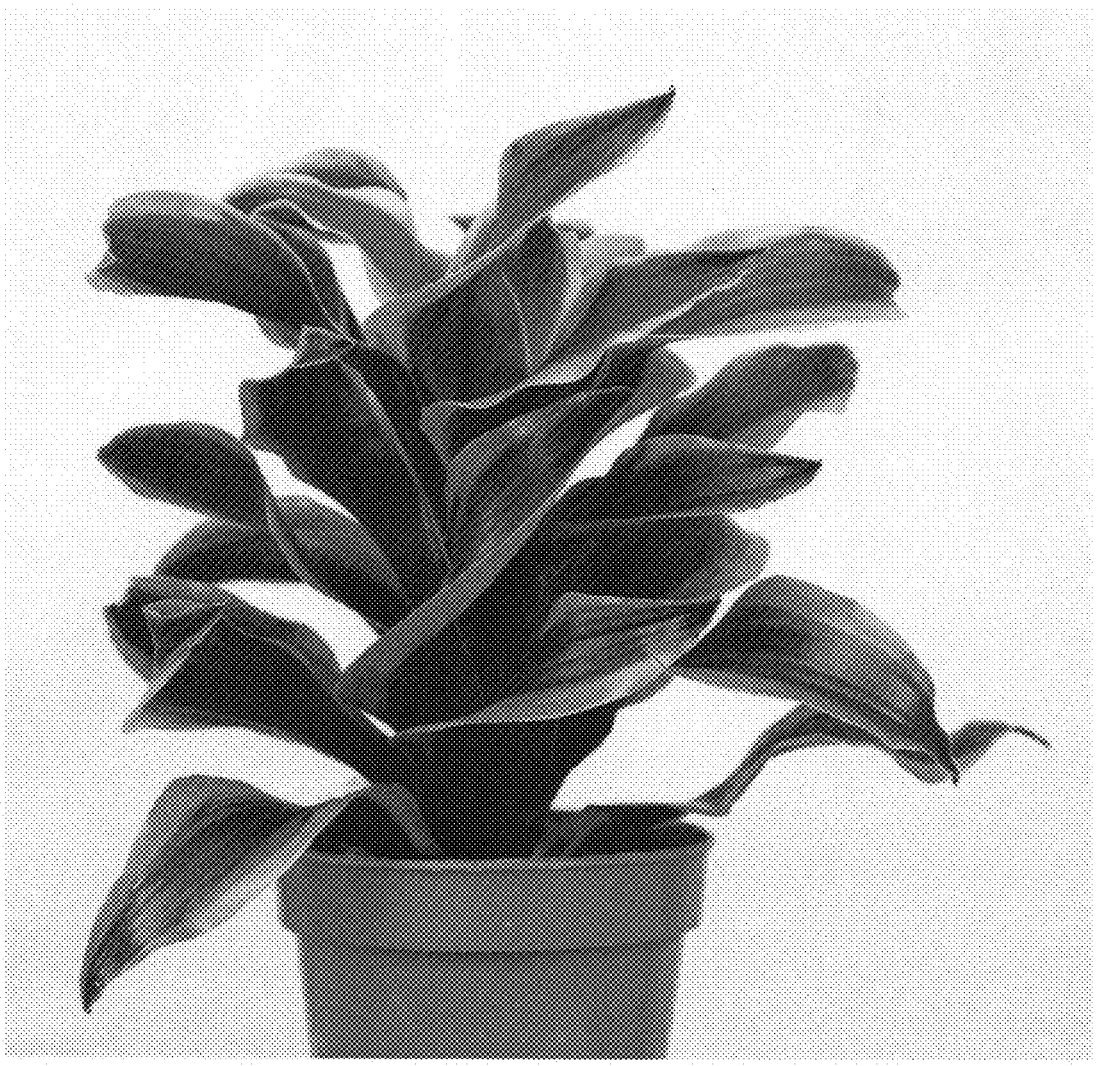
FIG. 1 shows, as nearly true as it is reasonably possible to make the same in color illustrations of this type, the typical foliage and growth characteristics of the new cultivar, 'Dradorco'. The plant shown is approximately 16 weeks old from a rooted cutting, potted into an 12 cm nursery pot, grown in a climate-controlled greenhouse in Roelofarendsveen, the Netherlands.
Figure 2:
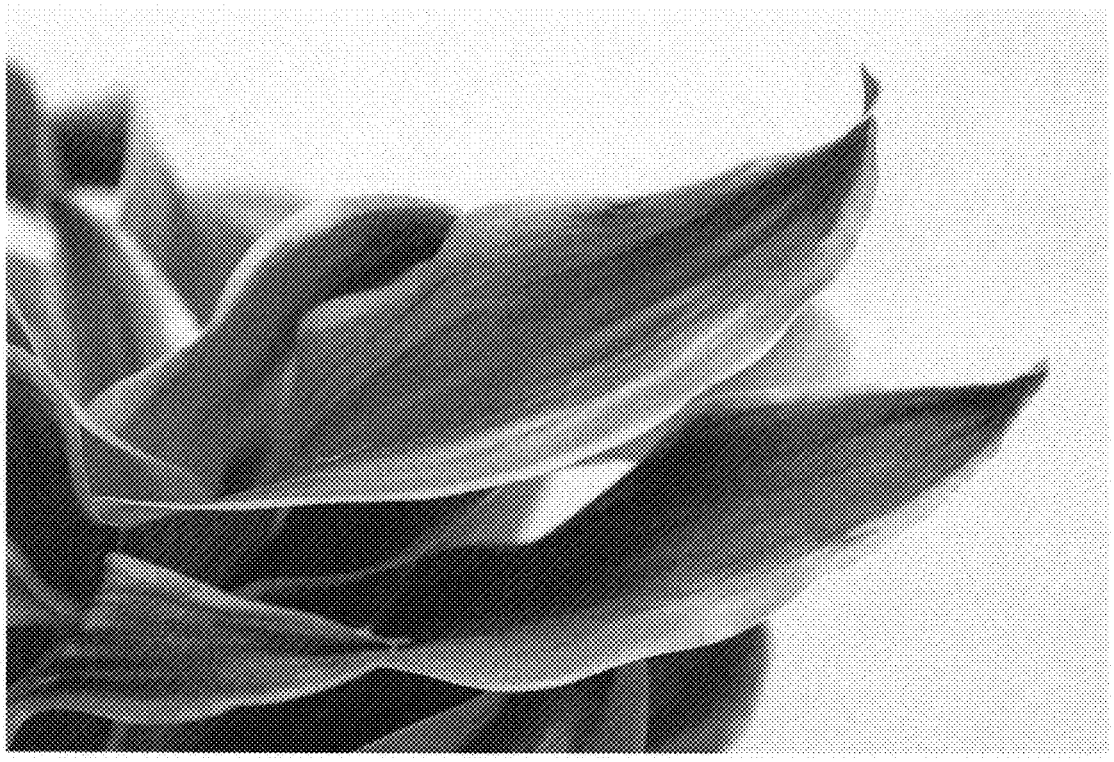
FIG. 2 shows, in full color, the typical foliage variegation of the plant in FIG. 1.
Figure 3:
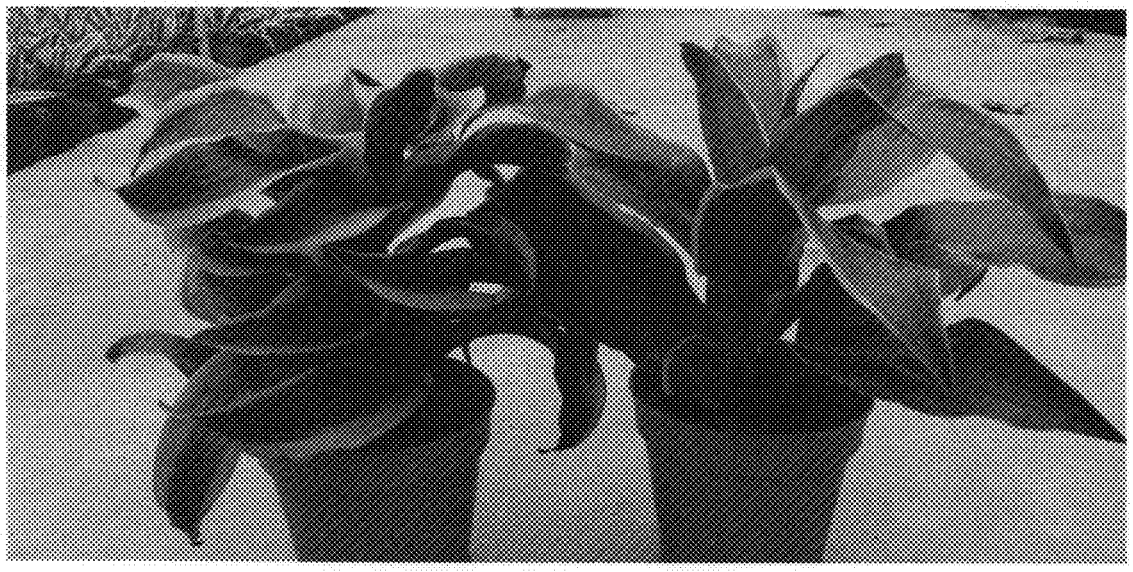
FIG. 3 shows, in full color, the plant in FIG. 1 on left with the most similar variety of common knowledge, *Dracaena fragrans* var. *compacta* 'Dorado' (not patented), on the right.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Dracaena fragrans* known as 'Dradorco', based upon observations of plants, approximately 16 weeks old from a rooted cutting, potted into a 12 cm nursery pot and grown under 70% shade during summer in a climate-controlled greenhouse in Roelofarendsveen, the Netherlands. Plants were maintained with overhead irrigation and regularly fertigated with a 1.2 EC solution. Plants were treated with an insecticide for the control of thrips. Observation data was recorded in September of 2015.

Those skilled in the art will appreciate that certain characteristics will vary with older or, conversely, with younger plants. 'Dradorco' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2007 edition.

A botanical description of 'Dradorco' and comparisons with the parent and the most similar variety of common knowledge are provided below.

General plant description:

*Growth rate*.—Moderate, approximately 7 cm per month.

*Growth habit*.—Upright; not free branching, typically growing with main stems from the base of the plant.

*Plant shape*.—Broad, obovate.

*Height*.—Average 20.4 cm in height.

*Width*.—Average 25.0 cm in width.

*Hardiness*.—USDA Zone 10.

*Propagation*.—Stem cuttings.

*Time to initiate roots*.—Approximately 35 days to initiate roots at approximately 23 degrees Centigrade.

*Time to produce a rooted cutting*.—Approximately 49 days to initiate roots at approximately 20 degrees Centigrade.

*Environmental tolerances*.—Moderately high drought tolerance once established; good heat tolerance.

*Pest resistance and susceptibility*.—Neither tolerance nor resistance to normal diseases and pests of *D. fragrans* have been observed.

Root system: Moderately thick, moderately fibrous, not fleshy; older roots greyed-orange, in between RHS 163A and 163B.

Stems:

*Branching characteristics*.—Not freely branched in nature; develops lateral branches only when manipulated by man by way of pruning. Naturally produces one main stem arising from the plant's base.

*Stem strength*.—Very strong.

*Stem diameter*.—Average 1.3 cm.

*Internode length*.—Average 0.6 cm.

*Stem texture*.—Glabrous, slightly glossy.

*Stem color*.—Yellow-Green, nearest to RHS 145C.

*Quantity of leaves per stem*.—Average 27.

Foliage:

*Attachment*.—Sheathing.

*Arrangement*.—Alternate and spirally.

*Attitude*.—Leaves in an average angle of 60 ° to stem (=0).

*Leaf shape*.—Broadly lorate; moderately curled and strongly spiraled or twisted along the midrib.

*Leaf apex*.—Long apiculate.

*Leaf base*.—Broad cuneate.

*Leaf length*.—Average 14.9 cm in length.

*Leaf width*.—Average 4.6 cm in width.

*Leaf margin*.—Entire; coarsely undulate.

*Texture, adaxial surface*.—Glabrous and glossy.

*Texture, abaxial surface*.—Glabrous and moderately glossy to glossy.

*Juvenile color, adaxial surface*.—Green, nearest to RHS NN137A, but darker; margined broad and irregular yellow-green, in between RHS N144A and N144B.

*Juvenile color, abaxial surface*.—A mixture of green, in between RHS 137B and 137C, and a lighter shade of green, RHS 143A; margined broad and irregular yellow-green, in between RHS N144A and N144B.

*Mature color, adaxial surface*.—A mixture of green, RHS NN137A, and a darker shade of green, nearest to RHS 139A, but darker; margined broad and irregular yellow-green, a mixture of RHS N144A, N144B, and N144C; margin color is nearest to RHS 144A on older leaves.

*Mature color, abaxial surface*.—Green, a mixture of RHS 137B, 137C and 143A; margined broad and irregular yellow-green, nearest to RHS N144A; margin color is nearest to RHS 144A on older leaves.

*Sheath dimensions*.—Approximately 1.8 cm long and 2.6 cm wide.

*Sheath texture, adaxial surface*.—Glabrous; glossy.

*Sheath texture, abaxial surface*.—Glabrous; matte.

*Sheath color, adaxial surface*.—Yellow-green, nearest to RHS 147D, to green-white, in between RHS147D and 157A.

*Sheath color, abaxial surface*.—Green, nearest to RHS 138C.

*Vein pattern*.—Parallel.

*Vein color, adaxial surface*.—Midrib is yellow-green, in between RHS 146B and 146C; secondary veins are the same color as surrounding leaf surface.

*Vein color, abaxial surface*.—Midrib is green, nearest to RHS 143A; secondary veins are the same color as surrounding leaf surface.

Flower: Flowering has not been observed.

Reproductive organs: Reproductive organs have not been observed.

Seed and fruit: Seed production has not been observed.

Comparisons with the parent: 'Dradorco' may be distinguished from its parent plant, '2004031C', by the following combination of characteristics:

1. 'Dradorco' exhibits a more compact growth habit and shorter stem internodes compared to that of '2004031C'.
2. The leaves of 'Dradorco' are approximately 50% shorter than the leaves of '2004031C'.
3. The leaves of 'Dradorco' exhibit strong spiraling, whereas the leaves of '2004031C' do not exhibit any spiraling.
4. 'Dradorco' exhibits a large area of golden coloration at and near the leaf margins, whereas the leaves of '2004031C' lack this coloration.

Comparisons with the most similar variety of common knowledge: Plants of the new cultivar 'Dradorco' may be distinguished from the commercial variety *Dracaena fragrans* var. *compacta* 'Dorado' by the following combination of characteristics:

1. 'Dradorco' exhibits a more compact growth habit and shorter stem internodes compared to that of 'Dorado'.
2. 'Dradorco' exhibits a large area of golden coloration at and near the leaf margins, whereas 'Dorado' exhibits a limited area of similar color, at and near the leaf margins.

That which is claimed is:

1. A new and distinct variety of *Dracaena fragrans* plant named 'Dradorco', substantially as described and illustrated herein.

* * * * *